(12) United States Patent
Supèr et al.

(10) Patent No.: US 8,795,694 B2
(45) Date of Patent: Aug. 5, 2014

(54) MICROPARTICLES COMPRISING PCL AND USES THEREOF

(75) Inventors: Henderikus Supèr, Utrecht (NL); Paul Willem Mijnen, Utrecht (NL); Pieter Gerard Zijlstra, Hilversum (NL); Dirk Wybe Grijpma, Hengelo (NL)

(73) Assignee: Aqtis I.P. B.V., Utrecht (NL)

( * ) Notice: Subject to any disclaimer, the term of this patent is extended or adjusted under 35 U.S.C. 154(b) by 314 days.

(21) Appl. No.: 12/670,518

(22) PCT Filed: Jul. 23, 2008

(86) PCT No.: PCT/NL2008/050506
§ 371 (c)(1),
(2), (4) Date: Apr. 30, 2010

(87) PCT Pub. No.: WO2009/014441
PCT Pub. Date: Jan. 29, 2009

(65) Prior Publication Data
US 2010/0215702 A1   Aug. 26, 2010

Related U.S. Application Data

(60) Provisional application No. 60/952,056, filed on Jul. 26, 2007.

(30) Foreign Application Priority Data

Jul. 26, 2007  (EP) .................................... 07113251

(51) Int. Cl.
 *A61K 9/14*  (2006.01)
(52) U.S. Cl.
 USPC ............................ 424/401; 424/489; 424/501
(58) Field of Classification Search
 USPC .......................................... 424/401, 422, 501
 See application file for complete search history.

(56) References Cited

U.S. PATENT DOCUMENTS

| 6,716,251 B1 * | 4/2004 | Asius et al. ................ 623/23.58 |
| 7,314,636 B2 | 1/2008 | Caseres et al. |
| 2003/0157187 A1 | 8/2003 | Hunter |
| 2005/0287180 A1 | 12/2005 | Chen |

FOREIGN PATENT DOCUMENTS

| EP | 0 711 548 B1 | 1/1998 |
| EP | 1754469 A1 | 2/2007 |
| EP | 1872803 A1 | 1/2008 |
| WO | WO-98/56431 A1 | 12/1998 |
| WO | WO-2004/041318 A1 | 5/2004 |

OTHER PUBLICATIONS

Chen et al., Polymer Degradation and Stability 67 (2000) 455-459.*
Blanco et al., Eur. J. Pharm. and Biopharm. 55 (2003) 229-236.*
International Search Report corresponding to PCT/NL2008/050506, dated Jun. 3, 2009, 10 pages.
International Preliminary Report on Patentability corresponding to PCT/NL2008/050506, dated Oct. 19, 2009, 11 pages.
Iooss, P et al: "A new injectable bone substitute combining poly($\varepsilon$-caprolactone) microparticles with biphasic calcium phosphate granules"; Biomaterials, Elsevier Science Publishers BV., Barking, GB, vol. 22, No. 20, Oct. 15, 2001, pp. 2785-2794.
Kim B S: "Novel therapeutic use of biodegradable polymer microspheres"; WPI / Thomson, Oct. 1, 2003, XP002458304, abstract.
Lin W-J et al: "A novel fabrication of poly($\varepsilon$-caprolactone) microspheres from blends of poly($\varepsilon$-caprolactone) and poly(ethylene glycol)s"; Polymer, Elsevier Science Publishers B.V, GB, vol. 40, No. 7, Mar. 1, 1999, pp. 1731-1735.

* cited by examiner

*Primary Examiner* — Michael G Hartley
*Assistant Examiner* — Robert Cabral
(74) *Attorney, Agent, or Firm* — Gilberto M. Villacorta; Sunit Talapatra; Foley & Lardner LLP

(57) ABSTRACT

The invention relates to a process for preparing PCL-comprising microparticles, to microparticles obtainable by said process, to gel hence obtained and to several uses of the gel such as for the preparation of a medicament for treating a skin abnormality or disfigurement, and/or for controlling bladder function and/or controlling gastric reflux and/or for treating erectile dysfunction and/or for treating vocal cords. The gel may also be used for cosmetic applications.

13 Claims, 3 Drawing Sheets

MICROPARTICLES COMPRISING PCL AND USES THEREOF

CROSS-REFERENCE TO RELATED APPLICATIONS

This application is a National Stage application of PCT/NL2008/050506, filed Jul. 23, 2008, which claims the benefit and priority of U.S. Provisional Application No. 60/952,056, filed Jul. 26, 2007 and European Patent Application No. 07113251.8, filed Jul. 26, 2007. The foregoing applications are incorporated by reference herein in their entirety.

FIELD OF THE INVENTION

The invention relates to a process for preparing microparticles comprising poly(ε-caprolactone) or polycaprolactone PCL, to the microparticles, to a biodegradable injectable gel and to several uses of the gel.

BACKGROUND OF THE INVENTION

With increasing age and/or as a consequence of certain diseases, the body's soft tissues, including muscle and fat can diminish, affecting appearance and/or diminishing function. For example, sphincter muscles that control many of the body's autonomic functions such as control of bladder function and gastric reflux diminish with age or disease. Several medical fillers have already been developed such as injectable bovine collagen. This filler has several drawbacks relating mainly to the risk of allergy, and the threat raised by the Kreutzfeld Jacob's disease. As an alternative for injectable bovine collagen, other fillers have been developed such as an implant comprising a particle suspension or emulsion of particles of a polymer comprising lactic acid and/or glycolic acid repeat units (US 2003/093157 or WO 98/56431).

However, the filler as disclosed in each of these patent applications has several drawbacks: the mixing and flowing properties (i.e. flow injectability) of a gel comprising such filler are not optimal due to final product constitution.

Therefore, there is still a need for a slowly resorbing biodegradable medical or cosmetical implant that will not cause any undesired reactions in the human body and that will have superior properties such as flowing properties because of essentially spherical microspheres which avoid aggregation, needle clogging, and nodule forming when injected.

DESCRIPTION OF THE INVENTION

Surprisingly, the inventors found that microspheres having superior properties, such as flowing properties may be obtained in an efficient and fast process wherein an initial mixture having a relatively high viscosity and comprising solubilized PCL and a surfactant is used. Each feature of this process is extensively detailed herein.

Process

In a first aspect, the invention relates to a process for preparing poly(ε-caprolactone) (PCL)-comprising microparticles wherein the process comprises the following steps:
 a1) solubilizing a PCL polymer, subsequently mixing the solubilized PCL polymer with a liquid comprising a surfactant, said liquid having a viscosity which is ranged between about 1 and about 400.000 cP,
 b) forming PCL-comprising microparticles from the solution obtained in a1).

In a second aspect, the invention relates to a process for preparing polycaprolactone (PCL)-comprising microparticles wherein the process comprises the following steps:
 a2) solubilizing a PCL polymer in dichloro methane (DCM) and/or in substantially pure Tween,
 b) forming PCL-comprising microparticles from the solution obtained in a2).

In one preferred embodiment, a process is encompassed by the invention which is according to both aspects defined above: this is a process wherein in step a) a PCL polymer is solubilized in DCM and/or in substantially pure Tween, said solubilized PCL polymer being subsequently mixed with a liquid comprising a surfactant, said liquid having a viscosity which is ranged between about 1 and about 400.000 cP. Subsequently as step b) PCL-comprising microparticles are formed from the solution obtained in a).

Steps a)

A first step a) of a process of the invention comprises or consists of or is a solubilization step.

Step a2)

A first step of a process of the invention consists of or is a solubilization step: a PCL polymer is solubilized in dichloromethane (DCM) and/or in substantially pure Tween. Accordingly, depending on the application intended for a gel comprising microparticles as later defined herein, the inventors found that the use of substantially pure Tween is particularly attractive when preparing a microparticle having a low to intermediate molecular weight, and due to the absence of an organic solvent. Preferably, low to intermediate molecular weight means a molecular weight which is ranged between about 1.000 and about 50.000 Mn (number average molecular weight), more preferably between about 1.000 and about 40.000 Mn, more preferably between about 5.000 and about 40.000 Mn, more preferably between about 1.000 and about 30.000 Mn, more preferably between about 10.000 and about 30.000 Mn, more preferably between about 20.000 and about 30.000 Mn and most preferably between about 1.000 and about 30.000 Mn. Therefore, in this second process of the invention, there are provided three preferred processes: one with the use of DCM, which is suited for providing microparticles with low to intermediate molecular weight or intermediate to high molecular weight. Preferably, intermediate to high molecular weight means a molecular weight which is ranged between about 30.000 and about 500.000 Mn, more preferably between about 40.000 and about 150.000 Mn, even more preferably between about 40.000 and about 100.000 Mn. Another preferred process uses substantially pure Tween, said process being suited for obtaining microparticles having a low to intermediate molecular weight. Finally, a third process uses a combination of DCM and substantially pure Tween.

Substantially pure Tween preferably means at least 80% Tween, or at least 90% Tween or approximately 100% Tween. Tween is a family of surfactants being esters of polyoxyethylene sorbitane. Tween 20, 40, 60 or 80 may be used. When substantially pure Tween is used in step a2), this solubilization step is preferably carried out close to or above the melting temperature of PCL. The temperature is approximately the melting temperature of PCL. Preferably, the temperature is ranged between about 50 and about 90° C., or between about 60 and about 90° C. More preferably, this temperature is of about 60° C. or about 80° C.

If DCM has been used in step a2), the solution obtained in a2) is subsequently added to a liquid comprising a surfactant in order to obtain a liquid comprising microparticles. A surfactant or tensoactive agent is a chemical that reduces the surface tension in a solution, allowing small, stable particles to form. A surfactant will stabilize the microparticles during their formation. Suitable surfactants include, but are not limited to, methyl cellulose (MC), polyvinylalcohol (PVA), polysorbates, such as polyoxyethylene sorbitans, or Pluronics™, preferably polyoxyethylene sorbitan monooleate, polyoxyethylene sorbitan trioleate, polyoxyethylene sorbitan monostearate, polyoxyethylene sorbitan tristearate, polyoxyethylene sorbitan monopalmitate, or polyoxyethylene sorbitan monolaurate, with polyoxyethylene sorbitan monooleate (Tween 80™), polyoxyethylene sorbitan monostearate (Tween 60™), and polyoxyethylene sorbitan monolaurate (Tween 20™) being preferred, and polyoxyethylene sorbitan monooleate (Tween 80™), being even more preferred. In a preferred embodiment, a surfactant is not a surfactant with limited biocompatibility such as polyvinylalcohol (PVA) which is described in EP 1 872 803 or in US 2003/0157187. A most preferred surfactant is MC among others because of its biocompatibility. Therefore, a process using DCM and subsequently MC as surfactant is expected to be more efficient than a process using DCM and subsequently PVA as surfactant: Due to its biocompatibility, there is no need to intensively wash the formed microparticles to get rid of the surfactant at the end of the process.

A liquid, preferably a liquid or gelly liquid comprising a surfactant is preferably defined as a liquid having a viscosity which is ranged between about 1 and about 400.000 cP, or between about 10 and about 100.000 cP, or between about 50 and about 100.000 cP, or between about 75 and about 50.000 cP, or between about 100 and about 50.000 cP or between about 100 and about 1.000 cP or between about 75 and about 1.000 cP. Most preferably, the viscosity is between about 75 and about 300 cP. Viscosity is preferably measured at room temperature or at the temperature where PCL is solubilized. In a preferred embodiment, a concentration of a surfactant, more preferably MC of between about 0.01 and about 5.0 w/w % is added, more preferably MC of between about 0.1 and about 5.0 w/w % is added, more preferably MC of between about 0.5 and about 2.5 w/w % is added, and most preferably about 1.0 w/w % of MC is added. Several types of MC are commercially available having distinct molecular weights: Mn=14000. Mn=41000, Mn=63000 or Mn=88000). Preferably, MC having a molecular weight of Mn=63000 is being used.

In a preferred embodiment, preferably about 1.0 w/w % of MC (Mn=63000) is used. Using such a high concentration of MC is attractive for the efficiency of the process and for the characteristics of the formed microparticles: the viscosity of the initial MC solution is high (100-120 cP). We surprisingly found that the addition of a large volume of a concentrated solution of PCL in DCM to the viscous MC solution can be done quite quickly (less than one minute) and as a consequence the viscosity of the obtained mixture is also quite high. The viscosity of the obtained mixture is approximately the same as the one of the MC solution. Vigourous stirring leads to the formation of microparticles that are substantially spherical as later identified herein. The concentration of PCL in DCM is later defined herein. Furthermore, the removal by evaporation of DCM can occur more quickly (within 1 to 3 hours) than in conventional extraction evaporation processes that use far less MC (Iooss P et al, (2001), 22: 2785-2794).

Step a1)

A first step of a process of the invention comprises a solubilization step. A solubilization step present in step a1) is preferably carried out as described in step a2). However, other liquids, solvents or surfactants may be used to solubilize a PCL polymer. Examples include aliphatic compounds, aromatic compounds, halogen containing compounds, chloroform, compounds not containing halogens, acetone, THF, toluene ethyl acetate or ethyl lactate, etc.

Subsequently, a solubilized PCL polymer is mixed with a liquid comprising a surfactant, said liquid having a viscosity which is ranged between about 1 and about 400.000 cP or between about 10 and about 100.000 cP. The viscosity is preferably ranged between about 10 and about 30.000 Cp, or preferably ranged between about 15 and about 20.000 cP, more preferably between about 20 and about 10.000 cP, even more preferably between about 40 and about 5.000 cP, even more preferably between about 50 and about 2.000 cP, even more preferably between about 75 and about 2.000 cP, even more preferably between about 75 and about 1.000 cP, even more preferably between about 100 and about 1.000 cP, even more preferably between about 75 and about 500 cP, or even more preferably between about 75 and about 400 cP and most preferably about 75 and about 300 cP. Viscosity is preferably measured at room temperature or at the temperature where PCL is solubilized.

A surfactant used in step a1) is preferably the same as in step a2). Such surfactants have been identified earlier herein. A preferred surfactant includes MC among others because of its biocompatibility. Preferred concentrations and types of MC have earlier been defined herein. Most preferred is used about 1.0 w/w % of MC (Mn=63000 cP). Using such a high concentration of MC gives a viscous solution that is attractive for the efficiency of the process and for the characteristics of the formed microparticles as later defined herein. Preferably, without wishing to be bound by any theory, the inventors believe that what matters is the viscosity of the liquid used in step a1) and/or of the formed solution at the end of step a1). Any or both of these viscosities are preferably high enough to facilitate step b) and to allow the formation at high yields of highly homogeneous microparticles as later defined herein. As exemplified in the examples, a yield of approximately 60-80% of particles having a diameter ranged between about 38 and 75 μm may be obtained which is quite advantageous. A yield of approximately 70-80% of particles having such diameter may even be obtained. Preferred viscosities of a liquid and of the obtained solution are both defined herein.

Step b)

Subsequently, PCL-comprising microparticles are formed from the solution or mixture obtained in a1) or a2). Depending a.o. on the identity of the solvent used in step a1) or a2) (a.o. DCM and/or Tween), distinct steps are carried out as explained below. If DCM has been used in step a1) or a2), the DCM is extracted from the PCL-containing microparticles dispersed in the viscous liquid by extraction evaporation. Extraction evaporation process is also known as evaporation extraction process and is well known to the skilled person and has been described for example in Journal of Controlled Release (Preparation of biodegradable microsheres and microcapsules, Journal of Controlled Release, (1991), volume 17:1-22). Due to the high viscosity of the mixture as defined herein, one may have to vigorously stir (approximately 1000 rpm as illustrated in the examples). Without being to be bound by any theory, we expect that due to vigorous stirring, air is incorporated into the mixture allowing foam to be produced, which is believed to facilitate the extraction/evaporation process. In addition, the extraction/evaporation process is facilitated by the fact that relatively low quantities of DCM (i.e. high ratio PCL/DCM as defined later herein) have to be extracted/evaporated. Said process has a duration of approximately 3 hours, whereas classical extraction/evaporation processes using a mixture having a much lower viscosity (see examples) are expected to have a much longer duration of more than 14 hours. During extraction evaporation, a substantial part till most of the DCM contained in the PCL-comprising microparticles is extracted into the water and evaporated at the surface.

If upon heating Tween has been used in step a1) or a2) as sole solvent, the microparticles are formed as a result of controlled cooling and stirring conditions. The end temperature is generally room temperature. The mixture may be heated up to 80° C. Stirring may be about 500 rpm. Controlled cooling may have a duration of 1 till 12 hours.

At the end of a process of the invention, microparticles are obtained which are substantially free of DCM and/or substantially pure Tween. Substantially free preferably means that less than 70 wt % of the initial DCM or substantially pure Tween is still present, more preferably less than 60 wt %, 50 wt %, 40 wt %, 30 wt %, 20 wt %, 10 wt %, 5 wt %, 2 wt %, 1 wt %, 0.5 wt %, 0.3 wt %, 0.2 wt % or even less than 0.1 wt %. In one embodiment, DCM and/or Tween are not detectable in the formed microparticles. DCM or Tween may be detected by means of Gas Chromatography (GC). The microparticles comprise or consist of a PCL polymer. Optionally, at the end of the process, microparticles may be washed in water one or several times to get rid of DCM and/or substantially pure Tween.

If DCM and Tween are combined as a solvent in the process of the invention, the process is preferably the same as when DCM is present as sole solvent.

In the context of the invention, a PCL polymer means a polymer comprising poly-ϵ-caprolacton or a polycaprolactone. PCL is a biodegradable, immunologically inactive, biocompatible and bioabsorbable synthetic polymer. A PCL polymer for use in the present invention may be obtained commercially or produced by methods well known to the skilled person. Preferably, a purified PCL polymer suitable for use in biomedical or cosmetic applications is employed. Polymers are molecules made up of low molecular weight repeating units called monomers. The process of joining monomers to produce polymers is called polymerization.

In the context of the invention, a polymer may be given all possible meanings known to the skilled person such as including a linear polymer, a copolymer, a block copolymer, a terpolymer or a blend of different types of homo-, co-, block co- or ter-polymers.

In a further preferred process, a copolymer of ϵ-caprolactone (CL) is used in step a1) or a2). Preferred copolymers of CL are: copolymers of CL with at least one compound selected from the group consisting of: L-lactide, D-lactide, DL-lactide, TMC (tri-methylene-carbonate, PEO (poly-ethylene oxide), glycolide and DO (dioxanone). When a copolymer of CL (a copolymer, a block copolymer) is used in a process where substantially pure Tween is used as sole solvent in step a2), the melting temperature of PCL is intended to mean the temperature at which the CL copolymer melts.

In a preferred process, a terpolymer of PCL is used in step a1) or a2). Preferred terpolymer of PCL are: copolymer of CL with one compound selected from the list consisting of: L-lactide, D-lactide, DL-lactide, TMC, PEO, glycolide and DO. When a terpolymer of PCL is used in a process where substantially pure Tween is used as sole solvent in step a2), the melting temperature of PCL is intended to mean the temperature at which the PCL terpolymer melts.

Alternatively, a terpolymer of PCL is a polymer of PCL with two compounds selected from the group consisting of: L-lactide, D-lactide, DL-lactide, TMC, PEO, Glycolide and DO. In addition to the above blends with homo/co,/block co-/ter-polymers with components selected from the group consisting of: L-lactide, D-lactide, DL-lactide, meso-lactide, TMC, PEO, glycolide and DO. Other CL co-polymers or blends may comprise Polyesters, polyethers, polycarbonates, copolyoxalates, poly (ortho carbonates), poly(acetals), polyanhydrides, pbt/peo copolymers (PolyActive™) and polyphosphazines.

In another preferred process, a PCL homopolymer is being used. A PCL homopolymer is advantageous since it is semi-crystalline. As such, it is form stable. In addition, it is hydrophobe and therefore, it may have a longer resorption time when used as a dermal filler than the corresponding resorption time of a non-semi-crystalline bioresorbable polymer. More preferably a PCL polymer is being used which does not comprise a second monomer being selected from the group consisting of glycolide, dioxanone, trimethylene carbonate and the lactides and combinations thereof.

In addition, as another preferred embodiment of the invention, a PCL polymer as used herein is replaced by another polymer. Such other polymer may be a polymer based on L-lactide, D-lactide, DL-lactide, meso-lactide, TMC, glycolide or dioxanone.

The properties of the polymer, of the obtained microparticles, and of the obtained gel all disclosed herein vary widely depending upon the intended application and are typically not critical. For injectable applications, the PCL comprising microparticles should be suitable for injection through a suitably-sized syringe.

In a preferred embodiment, a PCL polymer is added and will dissolve in DCM and/or substantially pure Tween at a concentration which is up to about 10% of DCM (as sole solvent or combined with Tween), up to about 30% of DCM (as sole solvent or combined with Tween) or up to about 50% in substantially pure Tween when Tween is used as a sole solvent on a weight basis. More preferably, a PCL polymer is added and will dissolve in DCM at a concentration which is up to about 25%, or up to 25%. This percentage depends largely on the molecular weight of the PCL used.

In a more preferred embodiment, the viscosity of a PCL DCM solution may be approximately ranged between 5 and 5 000 cp (measured at room temperature). This viscosity depends largely on the molecular weight of the PCL and on the PCL and DCM concentrations used. The ratio PCL/DCM (w/w) may be approximately ranged between 10 g PCL in 100 g DCM and 20 g PCL in 100 g PCL. This ratio is qualified of high compared to ratio previously used in the prior art.

The use of a high ration PCL/DCM as defined herein is advantageous since as less as possible DCM is present. Therefore, the evaporation process of DCM to obtain the microparticles of the invention is expected to be more rapid than in classical processes using more DCM than in the present invention.

Particle size and distribution is likely to be influenced by the identity of the surfactant used (MC is preferred), the PCL polymer (homopolymer is preferred), the PCL/solvent (DCM and/or substantially pure Tween) ratio (preferred ratios are given) and by the process conditions.

Microparticles

In a further aspect, the invention provides a microparticle obtainable by a process of the first and/or second aspect as outlined in the previous section.

These microparticles are not per se obtained using a process as described above as long as they have the desired characteristics as presented below. A process of the invention is one preferred process for obtaining these microparticles. Preferably, the microparticles of the invention have at least one of the following characteristics:

i) a diameter distribution which is ranged between 5 and 200 μm, more preferably between 20 and 150 μm, even more preferably between 30 and 90 μm, even more preferably between 25 and 75 μm, even more preferably between 38 and 75 μm, even more preferably between 25 and 50 μm.
ii) homogenous density, form and content (see FIG. 1 as an example): spherical shape and surface smoothness
iii) essentially spherical microspheres.

The homogenous characteristics (features i), ii) and/or iii)) of the microparticles of the invention is very attractive since it will confer optimal flowing properties to a gel derived there from (as presented in the following section): we expect there will be no aggregation in a syringe, no needle clogging when injected with a syringe. This homogenous characteristic represents an improvement over known gels used as implant. For example, the microparticles of the invention have more attractive properties than the ones as disclosed in EP 1 872 803 or in US 2003/0157187 preferably due to the use of a liquid comprising a surfactant, said liquid having a viscosity which is ranged between about 1 and about 400.000 cP in step a1), and/or preferably due to the use of MC as surfactant, more preferably 1% MC, even more preferably 1% MC (Mn=63000), and/or preferably due to the use of a higher ratio of PCL/DCM as defined herein, and/or preferably due to the way the extraction evaporation has been carried out.

As another example, the microparticles of the invention have more attractive properties than the ones as disclosed in Iooss (Iooss P et al, (2001), 22: 2785-2794) preferably due to the use of a liquid comprising a surfactant, said liquid having a viscosity which is ranged between about 10 and about 100.000 cP in step a1), and/or preferably due to the use of a higher ratio of PCL/DCM as defined herein, and/or preferably due to the use of specific type and concentration of MC as surfactant, more preferably due to the use of 1% MC, even preferably 1% MC (Mn=63000) and/or preferably due to the way the extraction evaporation has been carried out. The microparticles are so homogenous that they may also be named microspheres. The homogeneity of the microparticles (spherical shape and surface smoothness and any of the features as already defined as i), ii) and iii)) is due among others to a specific process of the invention, preferably due to the use of a liquid comprising a surfactant, said liquid having a viscosity which is ranged between about 1 and about 400.000 cP in step a1), and/or preferably due to an optimal ratio PCL/DCM as defined herein, and/or preferably due to a surfactant which is being used, more preferably 1% MC (Mn=63000) and/or preferably due to the way the extraction/evaporation process has been carried out.

A preferred diameter of the microparticles (microspheres) is ranged between 20 and 150 μm. A diameter larger than 20 μm is preferred since it minimizes direct phagocytosis by macrophages. A diameter smaller than 150 μm is preferred since it is expected to have even better flowing properties when present in a gel. Alternatively, a preferred diameter is ranged between 25 and 50 μm.

Surprisingly, the inventors found that microparticles comprising relatively low to intermediate molecular weight PCL as earlier defined herein are highly suitable to be used in the present invention. This low to intermediate molecular weight PCL comprising microparticles when present in a gel of the invention exhibits a relatively shorter resorption time than the one of a gel comprising microparticles with PCL of a intermediate to high molecular weight as defined later herein.

The microparticles may be stored in this dry state as freeze-dried, lyophilized or free-flowing powder and conserved for years under appropriate conditions. Lyophilization is advantageous since it facilitates sterilisation and storage. The molecular weight of the polymer and the inherent physical properties (among other spherical shape and surface smoothness, see at least one of the features as defined earlier herein as i), ii) and/or iii)) of the microparticles determine at least partly their in vivo degradation behaviour when present in a gel and upon injection in vivo.

Gel

In a further aspect, the invention relates to a biodegradable injectable gel comprising a microparticle as defined in the previous section and a carrier. A carrier may comprise a viscosity enhancing agent, a density enhancing agent, and/or a tonicity wetting enhancing agent. A viscosity enhancing agent may be selected from the group consisting of: sodium-carboxylmethyl cellulose (CMC), polyvinylpyrrolidone (PVP), methyl cellulose (MC), hydroxypropylmethylcellulose (HPMC). However, other viscosity enhancing agents may be used, as would be readily apparent to one skill in the art. CMC is preferred as a viscosity enhancing agent.

A density enhancing agent may be selected from the group consisting of: sorbitol, mannitol and fructose. Although other suitable density agents might be used.

A tonicity wetting agent may be a polysorbate (Tween 20, 40, 60, or 80). Other tonicity wetting agents may also be used. A gel disclosed herein may include varying amounts of a viscosity enhancing agent, a density enhancing agent and/or a tonicity wetting enhancing agent. In a preferred embodiment, a gel comprises: between about 0 and 8 wt % of a viscosity enhancing agent, and/or between about 0 and about 50 wt % of a density enhancing agent, and/or between about 0 and about 5.0 wt % of a tonicity wetting agent. More preferably, a gel comprises: between about 0.1 and 8 wt % of a viscosity enhancing agent, and/or between about 0 and about 50 wt % of a density enhancing agent, and/or between about 0 and about 5.0 wt % of a tonicity wetting agent.

A gel disclosed herein may include varying amounts of microparticles and may typically include from about 10 wt % to about 50 wt % of microparticles, from about 15 wt % to about 50 wt %, from about 25 wt % to about 45 wt %, from about 35 wt % to about 45 wt % microparticles. The amount of carrier is typically chosen to obtain a suspension having the desired flowing properties, i.e., of appropriate viscosity. The skilled person knows that depending on the type of application envisaged for a gel of the invention, a needle having specific characteristics may be used. For each type of needle used, the viscosity of the gel may have to be optimised in order to get desired flowing properties. As an example which is also a preferred embodiment, using a needle of 26-30 gauge, and CMC, a viscosity ranged between approximately 20 000 and 200 000 cp is appropriate. In a preferred embodiment, the carrier is a pharmaceutically or cosmetically acceptable carrier and/or a biologically medically acceptable carrier.

Biodegradable is synonymous to bioresorbable. The desired bioresorbability of the gel may vary depending on among other the type of PCL polymer used, the use/application envisaged. In a preferred embodiment, the gel of the invention is bioresorbable within 10 years or less than 10 years after the injection or within 5 years or less than 5 years after the injection or within 2 years or less than 2 years after the injection or within 1 year or less than 1 year after the injection.

The obtained gel comprises a suspension of microparticles as earlier defined and is more attractive than other known gels: the gel of the invention comprises microparticles that are essentially spherical with a smooth surface (having at least one of the following features as earlier defined herein i), ii) and/or iii)) and therefore the flowing properties of the gel are improved. Surprisingly, the inventors found that a gel comprising microparticles having a low to intermediate molecular weight may advantageously be used. A gel of the invention comprises a polymer which is more stable when injected in vivo (the kinetics of degradation are slower than for other polymers). A gel comprises microparticles and a carrier. A carrier is usually degraded, dissolved or resorbed within 3 to 4 months after the injection. The resorption time of the microparticles is dependent on the initial molecular weight of the PCL used. For example, microparticles comprising a PCL polymer having a low to intermediate molecular weight as earlier defined herein are expected to have a degradation or resorption time which is ranged between approximately 6 months and 2 years. As an example, a gel comprising microparticles comprising a PCL polymer having a molecular weight of about 10.000 Mn is expected to have a resorption time of approximately between 6 to 15 or 12 to 15 months depending on where it has been injected and on other characteristics of the microparticles. As another example, a gel comprising microparticles comprising a PCL polymer having a molecular weight of about 40.000 Mn is expected to have a resorption time of about approximately 18 to 24 or 20 to about 24 months depending on where it has been injected and on other characteristics of the microparticles. This gel may be used in several types of applications as defined below. A gel may be stored in a container in the form of a sterile suspension. Preferably, a container is a ready for use prefilled syringe. A syringe may also be provided as a two-compartment prefilled syringe, one containing the (freeze-dried) microparticles and the other containing a pharmaceutically acceptable carrier. If reconstituted extemporaneously e.g., by water or double distilled water, for injectable preparations, a gel (suspension) may then be applied by intradermal or subcutaneous injection. Alternatively, a container may be a vial. Here also as for a syringe, a vial may contain a gel of the invention ready to be used. Alternatively, a vial may contain in one compartment (freeze-dried) microparticles and in another compartment a pharmaceutically acceptable carrier.

The water used to reconstitute extemporaneously the gel in a syringue or in a vial is preferably distilled water, more preferably double distilled water, even more preferably sterile water. Most preferably, PBS (Phosphate Buffered Saline) is used.

A carrier may further comprise a component selected from the group consisting of a cryoprotectant and a buffering agent.

A cryoprotecting agent is a chemical which inhibits or reduces the formation of damaging ice crystals in biological tissues during cooling. Suitable cryoprotecting agents include, but are not limited to sugars and carbohydrates, such as d-mannitol, lactose, sucrose, fructose, sorbitol and dextran, with d-mannitol being preferred. The concentration of a cryoprotectant in the carrier of the gel may vary depending upon the intended application, the microparticle and the identity of the cryoprotectant chosen. A gel may typically comprise between about 0 and about 45% by weight of a cryoprotective agent, or between about 30% and about 40%.

A buffering agent is a chemical compound that is or compounds that are added to a solution to allow that solution to resist changes in pH as a result of either dilution or small additions of acids or bases. Effective buffer systems employ solutions which contain large and approximately equal concentrations of a conjugate acid-base pair (or buffering agents). A buffering agent employed herein may be any such chemical compound(s) which is pharmaceutically acceptable, including but not limited to salts (conjugates acids and/or bases) of phosphates and citrates. The gel may typically comprise between about 0 and about 0.2% by weight of a buffering agent, or between about 0.1% and about 0.15%. A preferred buffering agent is PBS.

In a further preferred embodiment, a gel comprising a micro-particle is for use as a medicament. A gel itself without any active ingredient, or preferably without any medicament comprised herein may be seen itself as a medicament. In this first case, a gel is preferably used as a filler or an implant to augment soft tissue in a mammal in a variety of treatments including treating a skin abnormality or disfigurement, controlling bladder function (treatment of urinary sphincter deficiency) and/or controlling gastric reflux (treatment of pyloric sphincter deficiency), cord vocal deficiency, congenital abnormalities, filling up gums for dental treatment. In all these uses, a mammal is preferably a human being. In all these uses, a gel is typically introduced into the tissue site to be treated or medicated typically by intradermal or subcutaneous syringe injection.

In a preferred embodiment, a gel is used as a filler and/or as an implant. In a more preferred embodiment, a gel is a dermal filler. Dermal filler may be used to correct skin abnormalities that forms a threat for the health of a subject such as a post-surgical skin abnormalities, or disfigurement like a burn. When a gel is used as a medicament and as a dermal filler depending on the application as a dermal filler, a PCL polymer has preferably a low to intermediate molecular weight or an intermediate to high molecular weight as earlier defined herein in step a1) or a2) of a process of the invention.

In another more preferred embodiment, a gel disclosed herein is used as an implant or filler to treat various sphincter deficiencies such as urinary incontinence (control of bladder function). Loss of bladder control may be due to stress due to physical movement (coughing, sneezing, exercising) and/or to urge or leakage of large amounts at unexpected times, including sleep. All types of incontinences may be treated using a gel of the invention regardless of the patient's age. Continence is dependent upon a compliant reservoir and sphincter efficiency that has 2 components: (1) the involuntary smooth muscle on the bladder neck; and (2) the voluntary skeletal muscle of the external sphincter.

Therefore, a gel of the invention may be added to localize compression to the sphincter muscle or urethra, thereby reducing the lumen size through one or more injections of the gel and thus substantially reduce or eliminate urinary stress incontinence. In these instances a gel may be inserted by injection into urethral or periurethral tissue. Thus, a typical procedure involves injecting a gel with the aid of a cystoscope into the tissues around the neck of the bladder creating increased tissue bulk, and subsequent coaptation of the urethral lumen. A gel adds bulk and helps to close the urethra to reduce stress incontinence. The injection may typically be repeated periodically for optimal results.

In another more preferred embodiment, a gel is used as a filler or as an implant for controlling gastric reflux (to treat a deficiency of the pyloric sphincter). Gastroesophageal reflux disease (GERD) involves the regurgitation of stomach gastric acid and other contents into the oesophagus or diaphragm. 70% of reflux episodes occur during spontaneous relaxations of the lower oesophageal sphincter, or due to a prolonged relaxation after swallowing. 30% occur during periods of low sphincter pressure. The primary symptom is heart burn (30 to 60 minutes after meals). Atypical manifestations of GERD include: asthma; chronic cough; laryngitis; sore throat; and non-cardiac related chest pain. GERD is a lifelong disease that requires lifestyle modifications as well as medical intervention.

Therefore, a gel of the invention may be injected to add bulk and localize compression to the lower oesophageal sphincter. Thus, a typical procedure involves injecting a gel with the aid of a endoscope into the tissues around the lower oesophageal sphincter creating increased tissue bulk, and subsequent coaptation, normalizing sphincter pressure. A gel adds bulk and helps to close the sphincter to reduce reflux. The injection may be repeated yearly for optimal results. A gel may be injected using local aenesthesia.

When a gel is used as a medicament for controlling bladder function and/or gastric reflux, a PCL polymer used has preferably an intermediate to high molecular weight as earlier defined herein in step a1) or a2) of a process of the invention. This is preferred since the gel hence used will stay present at the injected site much longer (lower in vivo degradation rate) and the surgical intervention will not have to be repeated often.

In another more preferred embodiment, a gel is used as a filler or as an implant for treating erectile dysfunction (ED) that may affect men of all ages. A gel of the invention may be used for treating ED. A typical procedure involves injecting a gel directly at the deep fascia throughout the length of the corpus cavernosum.

In another more preferred embodiment, a gel is used as a filler or as an implant for treating vocal cords. A gel of the invention may be used for intra-cordal injections of the laryngeal voice generator by changing the shape of this soft tissue mass.

It is further encompassed by the present invention that a gel itself when seen as a medicament further comprises an active ingredient, which is also preferably a medicament. As used herein, a "medicament" may be any bioactive composition, pharmaceutical, drug or compound which one desires to administer to the site of the injection of a gel. In this case, a medicament added to a gel may facilitate the function of a gel and may comprise an anaesthetic to decrease the pain or discomfort associated with injecting a gel or a composition that facilitates the integration of a PCL or of a microparticle or decreases the trauma to the injection site. In one preferred embodiment, a medicament is added to the gel. Exemplary anesthetics include but are not limited to lidocaine, xylocalne, novocaine, benzocaine, prilocalne, ripivacaine, and propofol. Other medicaments that can be employed in a gel disclosed herein include: a peptide, a tissue regeneration agent, an antibiotic, a steroid, fibronectin, a cytokine, a growth factor, an analgesic, an antiseptic, alpha-, beta-, or gamma-interferon, erythropoietin, glucagons, calcitonin, heparin, interleukin-1, interleukin-2, filgrastim, cDNA, DNA, proteins, peptides, HGH, luteinizing hormone, atrial natriuretic factor, Factor VIII, Factor IX, and follicle-stimulating hormone. A medicament is often added to a gel just prior to the injection during activation mixing with a carrier as earlier defined herein. Typically an active ingredient or a medicament is present in the microspheres which might be introduced into a gel, said gel may subsequently be injected.

Alternatively, in another preferred embodiment, a medicament present in a gel is not present for facilitating the function of a gel. In this case, a gel is seen as a controlled delivery system for any known or to be discovered medicament.

In another preferred embodiment, a gel is a cosmetic gel. A cosmetic gel may be used as a dermal filler. Within this preferred embodiment, a gel having optimal characteristics is obtained when carrying out a process of the invention when preferably a liquid comprising a surfactant, said liquid having a viscosity which is ranged between about 1 and about 400.000 cP is used in step a1), and/or preferably when a high ratio of PCL/DCM as defined herein is used, and/or preferably when MC is used as a surfactant, more preferably approximately 1% MC, even more preferably approximately 1% MC Mn=63000 and/or preferably when the extraction evaporation has been preferably carried out as earlier defined herein. Within this preferred embodiment, a PCL polymer is preferably a PCL homopolymer. Within this preferred embodiment, a gel does not comprise any active ingredient or medicament. When a gel is used as a cosmetic gel as a dermal filler, a PCL polymer has preferably a low to intermediate molecular weight as earlier defined herein in step a2) of a process of the invention. A gel may be used in the cosmetic treatment of scars, wrinkles, and facial fat loss. A gel of the present invention may be used to fill and smooth out soft tissue defects such as pock marks or scars (such as chicken pox or acne scars, congenital anomalies (such as cleft lips) and wrinkles Scars may be of any origin: disease, post-surgical, burn. A gel may also be used as bulking agents to augment facial tissue or fat loss in the human. The anatomical area for the efficient use of a gel may be the skin preferably the skin of the facial region: epidermis and/or subcutaneous. Depending of the specific cosmetic application envisaged, the site of injection may vary: sites for treating acne scars and fine facial lines, deeper sites for treating wrinkles, creases and modelling of facial profile, and deeper sites for treating lipodystrophy.

Use of the Gel

A further aspect of the invention relates to a use of a gel of the invention for the preparation of a medicament for treating a skin abnormality or a skin disfigurement or for controlling bladder function and/or for controlling gastric reflux and/or for treating erectile dysfunction and/or for treating vocal cords.

Another use of a gel of the invention is a use of a cosmetic gel of the invention as earlier herein defined in cosmetic applications.

All the features of these uses have already been defined in the former section entitled "gel".

In this document and in its claims, the verb "to comprise" and its conjugations is used in its non-limiting sense to mean that items following the word are included, but items not specifically mentioned are not excluded. In addition the verb "to consist" may be replaced by "to consist essentially of" meaning that a product or a composition or a gel or a microparticle as defined herein may comprise additional component(s) than the ones specifically identified, said additional component(s) not altering the unique characteristic of the invention. In addition, reference to an element by the indefinite article "a" or "an" does not exclude the possibility that more than one of the element is present, unless the context clearly requires that there be one and only one of the elements. The indefinite article "a" or "an" thus usually means "at least one". The word "about" or "approximately" when used in association with a numerical value (about 10) preferably means that the value may be the given value of 10 more or less 1% of the value.

All patent and literature references cited in the present specification are hereby incorporated by reference in their entirety.

The following examples are offered for illustrative purposes only, and are not intended to limit the scope of the present invention in any way.

EXAMPLES

Protocol for the synthesis of the microspheres/microparticles and the suspension of these particles in a gel comprising a carrier which is ready for use is described below.
1. Microspheres are prepared using a classical solvent evaporation technique or by means of a solventless synthesis technique in order to obtain the desired properties.
2. The gel is prepared with a required viscosity using known preparation techniques, after which the microspheres are suspended in the gel by means of appropriate mixing.
3. Syringes are then filled with the sterilised gel suspension in a controlled atmosphere.

The following examples can be used or combined in order to obtain a suspension of microparticles comprised of polymers or blends mentioned afore in a ready for use application or (freeze-dried) vial application.

Example 1

10 to 20 grams of Mn 10000 or Mn 42500 PCL is dissolved in DCM (10 to 20 w/w %). This solution is dispersed in 1000 ml water containing 0.1-5% MC. By means of ferocious stirring (1000 rpm) microparticles with an average diameter of 40 μm are obtained by solvent extraction as described in the publication cited in the description. The microspheres obtained are filtrated, washed and dried. Subsequently, 10 to 50% of the microspheres are dispersed in the CMC (0.1 to 5%) or MC (0.1 to 5%) gel by moderate mixing and processed further.

Example 2

Figure 1:
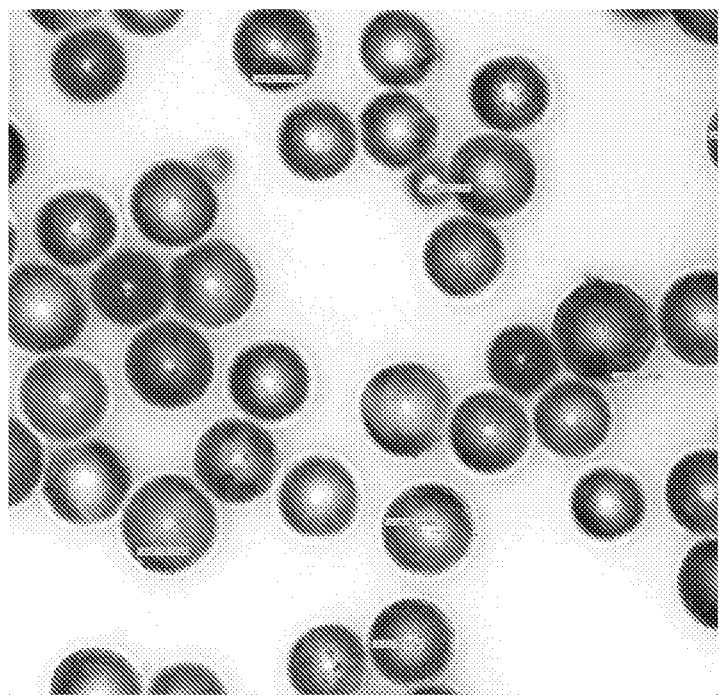
FIG. 1. Microscopic photography of microspheres as prepared in example 2.

10 to 20 grams of Mn 42500 PCL is dissolved in DCM (10 to 20 w/w %). This solution is dispersed in 1000 ml water containing 0.8% MC. By means of ferocious stirring (1000 rpm) microparticles with an average diameter of 60 μm are obtained by solvent extraction as in example 1. The microspheres obtained are filtrated, washed and dried. Subsequently, 10 to 50% of the microspheres are dispersed in the CMC (0.1 to 5%) or MC (0.1 to 5%) gel by moderate mixing and processed further. A microscopic photography of the microspheres prepared in example 2 is shown in FIG. 1.

Example 3

40 g to 80 grams of Mn 10000 PCL is dissolved in pure Tween 20, 40, 60, or 80 by means of heating to 70-90 C and stirring (600-1000 rpm) after which the microspheres are obtained due to phase separation and controlled cooling towards 5 C within 30 min. The obtained microspheres obtained are filtrated, washed and dried. Average distribution 45 um, yield 75% within the required range Subsequently, 10 to 50% of the microsheres are dispersed in the CMC (0.1 to 5%) or MC (0.1 to 5%) gel by moderate mixing and processed further.

Additional Examples

The invention relates to an efficient and effective process for the preparation of biodegradable microspheres. A key issue is the use of surfactant solutions with relatively high concentrations and viscosities. The inventions lead to the formation of homogeneous particles with smooth surfaces in a desired size range of approximately 38 to 75 μm.

A) In one process of the invention as extensively exemplified in example 4, the viscous polymer solution is rapidly added to a vigorously stirred solution of a surfactant in water. Particles are formed upon vigorous stirring of the mixture and evaporation of the solvent. A volatile solvent such as DCM is preferred. This rapid addition is possible due to the high viscositie of the vigorously stirred surfactant solution in water. Vigorous stirring also allows short solvent evaporation times before the particles can be collected and further processed. As this is efficient, this is advantageous and desired.

To be able to recover the polymer microspheres, essentially all (or at least the majority) of the polymer solvent needs to be removed. Only then will the spherical polymer particles harden (and in the case of crystallisable particles, will they be able to crystallize)

The time required to evaporate and remove the solvent can be determined in several ways:
- the dispersion that had cooled due to evaporation of the solvent has warmed up again to ambient temperatures
- the dispersion of PCL microspheres turns white upon crystallization of the polymer
- with surfactants like MC, a foam on the surface of the surfactant solution is formed when DCM evaporates. This foam disappears as essentially all DCM has evaporated
- the microspheres do not coagulate upon standing B) In another process of the invention as extensively exemplified in example 7, the PCL polymer is dissolved upon heating in a relatively viscous surfactant (solution) such as Tween. Here droplets of polymer form upon dispersion of the molten polymer in the surfactant solution due to vigorous stirring of the mixture. Particles form after upon continued stirring and (controlled) cooling of the mixture to room temperature. This process is very efficient, as no volatile solvents are required.

Characteristics of the processes:
desired particle size range: we collected fractions of 38-75 µm.
efficient process: short evaporation times when using DCM and high yields in desired size range
effective process: essentially spherical shape particles with smooth surfaces, leading to good injectability of the particles Injectable gels could readily be formed from microspheres prepared according to the invention by mixing. Microsphere volumes of up to 50% could be homogeneously mixed into carboxymethyl cellulose gels (CMC, Aqulon from Hercules solutions in water or in phosphate buffered saline) by slow stirring.

Example 4

Experiments of the Invention

Preparation of Microspheres Using PCL Solutions in DCM and MC Solutions in Water Poly(ε-caprolactone) (PCL) microspheres were prepared by vigorously mixing PCL solutions in dichloromethane (DCM) into methylcellulose (MC) solutions in water, followed by evaporation of DCM.

Different amounts of PCL obtained from Sigma Aldrich with Mn=10000 g/mol were dissolved in DCM. Of these solutions 100 g was added to 1000 g of solutions of MC in water in a 2 liter beaker within 2 seconds while vigorously stirring at 1000 rpm. MC obtained from Colorcon Ltd. of different molecular weights (Mn=14000 g/mol, Mn=41000 g/mol and Mn=63000 g/mol) was employed.

Within three hours continuously stirring vigorously at room temperature, essentially all DCM had evaporated. Stirring was discontinued, and the microspheres that had formed were allowed to settle at the bottom of the beaker. The supernatant was removed and the microspheres were washed with water. Using stainless-steel sieves, the microspheres were sieved in the wet state and the fraction with diameters between 38 and 75 micrometer was collected.

The microspheres were vacuum-dried at room temperature, and the yield was determined gravimetrically. Light microscopy (magnification 10×) was employed to analyze the morphology of the obtained microspheres.

A series of experiments, where the concentration of the PCL solution and the characteristics of the MC solution were varied, was conducted. The results are presented in Table 1.

From Table 1 it can be seen that when using a relatively high viscosity MC solution, smooth spherical particles can be obtained efficiently. Furthermore, a high concentration of the PCL solution leads to high yields of PCL particles of the desired particle sizes.

Example 5

Experiments of the Invention

Preparation of Microspheres Using PLLA Solutions in DCM and MC Solutions in Water Poly(L-lactide) (PLLA) microspheres were prepared by mixing a PLLA solution in dichloromethane (DCM) into a methylcellulose (MC) solution in water, followed by evaporation of DCM.

An amount of 10 g of PLLA obtained from Purac Biochem (with intrinsic viscosity in chloroform of 2.3 dl/g) was dissolved in 100 g of DCM. Of this solution 100 g was added to 1000 g of a solution of MC in water in a 2 liter beaker within 2 seconds, while vigorously stirring at 1000 rpm. MC with Mn=63000 g/mol was obtained from Colorcon Ltd.

Within three hours continuously stirring vigorously at room temperature, essentially all DCM had evaporated. Stirring was discontinued, and the microspheres that had formed were allowed to settle at the bottom of the beaker. The supernatant was removed and the microspheres were washed with water. Using stainless-steel sieves, the microspheres were sieved in the wet state and the fraction with diameters between 38 and 75 micrometer was collected.

The microspheres were vacuum-dried at room temperature, and the yield was determined gravimetrically. Light microscopy (magnification 10×) was employed to analyze the morphology of the obtained microspheres.

TABLE 1

Preparation of PCL microspheres upon mixing PCL solutions in DCM in MC solutions in water while vigorously stirring.

| [PCL] (g/100 g DCM) | Mn of MC (g/mol) | [MC] (wt %) | Viscosity of MC solution (cP) | PCL recovered as particles of 38-75 µm (wt %) | PCL particle shapes | PCL particle surfaces |
|---|---|---|---|---|---|---|
| 10 | 14000 | 0.8 | 13 | 6.6 | irregular | rough |
| 10 | 41000 | 0.8 | 56 | 35.2 | irregular | rough |
| 10 | 63000 | 1.1 | 120 | 51.6 | spherical | smooth |
| 20 | 63000 | 1.1 | 120 | 74.0 | spherical [a] | smooth [a] |

Figure 2:
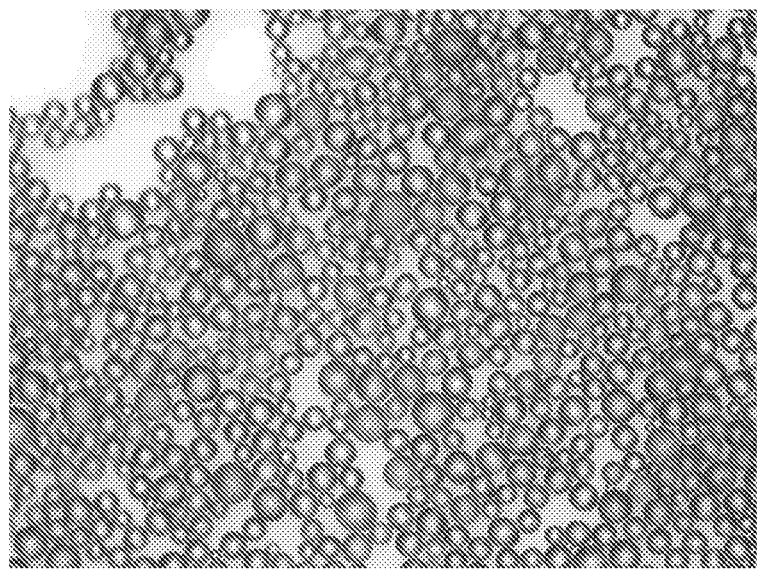
FIG. 2. PCL microspheres prepared using a PCL (Mn=10000 g/mol) solution in DCM and an MC (Mn=63000 g/mol) solution in water. [PCL] is 20 g/100 g DCM, [MC] is 1.1 wt %, see Table 1. Light microscopy image, magnification 10×.

[a] see light microscopy image presented in FIG. 2.

TABLE 2

Preparation of PLLA microspheres upon mixing a PLLA solution
in DCM in an MC solution in water while vigorously stirring.

| [PLLA]<br>(g/100 g DCM) | Mn of MC<br>(g/mol) | [MC]<br>(wt %) | Viscosity of MC<br>solution (cP) | PLLA recovered as<br>particles of 38-75 μm<br>(wt %) | PLLA particle<br>shapes | PLLA particle<br>surfaces |
|---|---|---|---|---|---|---|
| 10 | 63000 | 1.1 | 120 | 64.0 | spherical | smooth |

This Table 2 shows that it is possible to also prepare PLLA microspheres efficiently. When using a high viscosity MC solution, smooth spherical PLLA microspheres of the desired particle sizes can be in high yields.

Example 6

Comparative Experiments

Preparation of Microspheres Using PCL and CL Copolymer Solutions in DCM and Surfactant Solutions in Water
I Typical Data from the Literature:
The preparation of PCL and CL copolymer microspheres has been described in the scientific and patent literature. For example in publications by Hunter (US2003/0157187A1), Erneta and Wu (EP1872803A1) and Ioos et al. (Biomaterials 22 (2001) 2785-2794) it is described that addition of PCL solutions in DCM to solutions of polyvinyl alcohol (PVA) or MC in water can lead to the formation of PCL microspheres.

To prevent coagulation of the PCL solution in the stirred aqueous medium, the conditions employed involve addition of the PCL solutions in DCM over relatively long periods of time, and long DCM evaporation times to allow the dispersed PCL particles to harden. Only then are the formed spherical PCL microspheres stable enough to be collected. PCL microspheres were prepared using various experimental setups, and different PCL and CL copolymers and surfactant concentrations, addition rates and solvent evaporation times.
Hunter (Example 41 in US2003/0157187A1):
PCL: Mn=25000-45000 g/mol; PCL concentration in DCM: 9.5 wt/vol %; PVA: Mn=12000-18000 g/mol; 2 ml of the polymer solution were poured into 100 ml of the aqueous surfactant solution at a stirring rate of 1000 rpm; addition time of polymer solution: 120 min; particles were centrifuged and washed with water; microspheres with sizes ranging from 30-100 micrometer were obtained. The particles were spherical, but had a rough or pitted morphology.
Erneta and Wu (Examples in EP1872803A1):
Semi-crystalline CL copolymers: molar masses between 5000 and 25000 g/mol; polymer concentration in DCM: 4 to 7.5 wt/vol %, PVA: Mn is not indicated; approximately 275 g of solution was poured into approximately 1500 ml of the aqueous surfactant solution while stirring at rates close to 250 rpm; addition times of polymer solution: up to 19 min; DCM evaporation times 14 to 16 hrs; fraction of recovered microspheres with sizes of 38-75 micrometer is up to 71%; surface morphology is not indicated.
Iooss (Biomaterials 22 (2001) 2785-2794):
PCL: Mw=150000; MC: Methocel A15LV with Mn=14000; PCL concentration in DCM: 6.7 to 9.1 wt/vol %; 15 ml of solution is poured into the aqueous MC solution while stirring at 400-600 rpm during 1 hour; DCM is removed by extraction in large volume (1000 ml) of water; fraction of recovered PCL particles with sizes smaller than 80 micrometer vary between approximately 1 and 40%.

An overview of this data is presented in Table 3.

TABLE 3

Overview of literature data on PCL and CL copolymers microspheres prepared by
mixing polymer solutions in DCM in stirred surfactant solutions in water.

| | [polymer] in<br>DCM | [surfactant] in<br>water (wt %) | polymer solution<br>adding time (min) | DCM evaporation<br>time (hrs) | particle<br>shapes | particle<br>surfaces |
|---|---|---|---|---|---|---|
| Hunter | 9.5 wt/vol % | PVA, 1.0 | 120 | 2 | spherical | rough |
| Erneta, Wu | 4 to 7.5 wt % | PVA, 3.0 | 12 to 19 | 14 to 16 | — | — |
| Iooss | 9.1 wt/vol % | MC, 0.1 | 60 | 1 | no | smooth |

II Preparation of Microspheres Using PCL Solutions in DCM and Surfactant Solutions in Water. The Polymer and Surfactant Concentrations are as Described in Literature.
An amount of 80 g of PCL (obtained from Sigma Aldrich with Mn=10000 g/mol) was dissolved in 800 g DCM. Of this solution 100 g were added to 1000 g of solutions of PVA or MC surfactants in water in a 2 liter beaker within 2 seconds while vigorously stirring at 1000 rpm. In the experiments PVA with Mn=9000-10000 g/mol obtained from Sigma Aldrich and MC obtained from Colorcon Ltd. with Mn=14000 g/mol were employed.

Within three to four hours continuously stirring vigorously at 1000 rpm at room temperature, essentially all DCM had evaporated. Stirring was discontinued, and the microspheres that had formed were allowed to settle at the bottom of the beaker. The supernatant was removed and the microspheres were washed with water. Using stainless-steel sieves, the microspheres were sieved in the wet state and the fraction with diameters between 38 and 75 micrometer was collected.

The microspheres were vacuum-dried at room temperature, and the yield was determined gravimetrically. Light microscopy (magnification 10×) was employed to analyze the morphology of the obtained microspheres.

A comparative experiment was conducted as described in the literature by Erneta and Wu (EP1872803A1). Here 270 g of a 7.5 wt % PCL solution in DCM was added over a period of 12 minutes to 1500 ml of solution of 3.0 wt % PVA in water while stirring at 240 rpm. Before collecting the microspheres, DCM was let to evaporate under continued stirring for 16 hrs.

The results are compiled in Table 4.

TABLE 4

Preparation of PCL microspheres upon mixing PCL solutions in DCM in MC solutions in water while stirring.

|  | [PCL] in DCM (wt %) | [surfactant] in water (wt %) | Viscosity of surfactant solution (cP) | Stirring rate (rpm) | PCL recovered as particles of 38-75 μm (wt %) | particle shapes | particle surfaces |
|---|---|---|---|---|---|---|---|
| Hunter | 10 | PVA, 1.0 | 13 | 1000 | 44.0 | irregular [a] | rough [a] |
| Erneta, Wu | 10 | PVA, 3.0 | 14 | 1000 | 23.2 | irregular [b] | rough [b] |
| Erneta, Wu | 7.5 | PVA, 3.0 | 14 | 240 | 20.0 | spherical | smooth |
| Iooss | 10 | MC, 0.1 | 15 | 1000 | 1.1 | irregular [c] | rough [c] |

Figure 3:
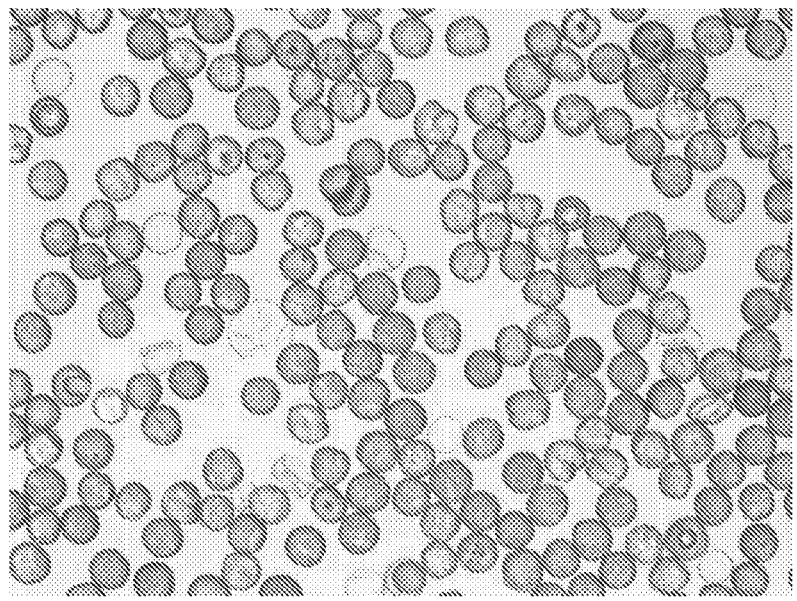
FIG. 3. PCL microspheres prepared using a 10 wt % PCL solution in DCM and a 1.0 wt % PVA solution in water while vigorously stirring at 1000 rpm. See Hunter, Table 4. Light microscopy image, magnification 10×.
Figure 4:
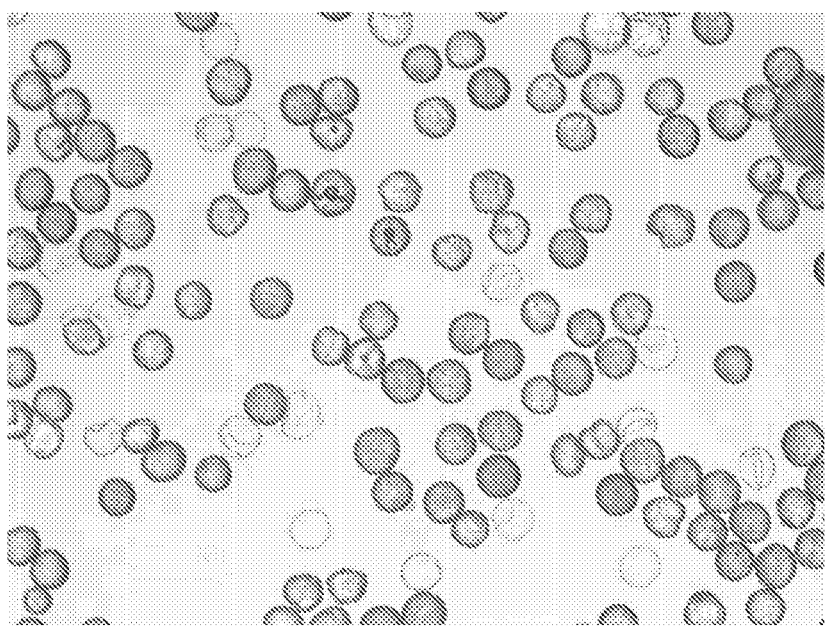
FIG. 4. PCL microspheres prepared using a 10 wt % PCL solution in DCM and a 3.0 wt % PVA solution in water while vigorously stirring at 1000 rpm. See Emeta and Wu, Table 4. Light microscopy image, magnification 10×.
Figure 5:
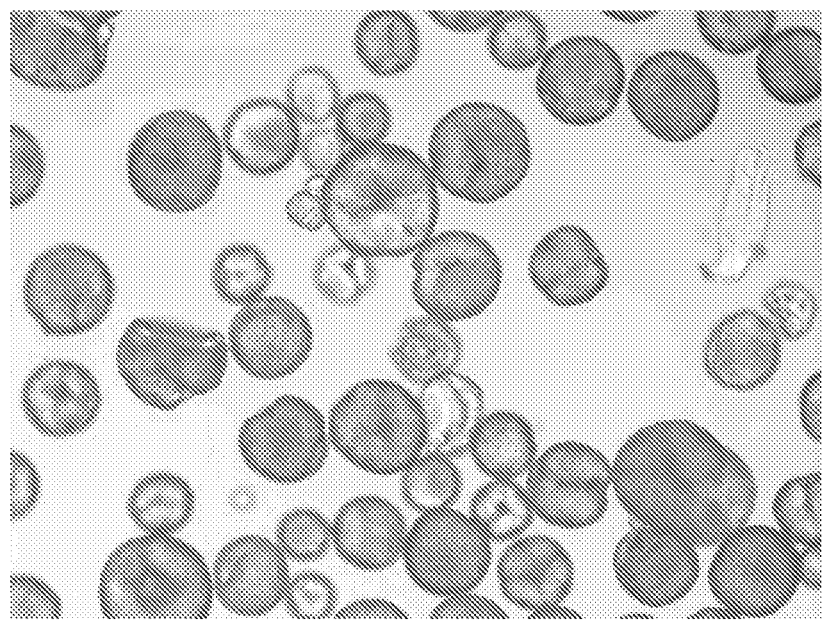
FIG. 5. PCL microspheres prepared using a 10 wt % PCL solution in DCM and a 0.1 wt % MC solution in water while vigorously stirring at 1000 rpm. See Iooss, Table 4. Light microscopy image, magnification 10×.

The polymer and surfactant concentrations are typical of those used in experiments described in literature.
[a] see light microscopy images presented in FIGS. 3.
[b] see light microscopy images presented in FIGS. 4.
[c] see light microscopy images presented in FIGS. 5.

From Table 4 it follows that using typical polymer and surfactant concentrations described in literature it is not possible to efficiently prepare particles with the desired characteristics. At these low viscosities of the surfactant solutions, it apparently is necessary to add the polymer solution over longer periods of time, to stir at relatively low speeds and to evaporate DCM for longer time periods to efficiently prepare particles with the desired characteristics.

III Preparation of Microspheres Using PCL Solutions in DCM and Viscous Surfactant Solutions in Water.

PCL microspheres were prepared by vigorously mixing PCL solutions in dichloromethane (DCM) into surfactant solutions in water, followed by evaporation of DCM.

Different amounts of PCL obtained from Sigma Aldrich with Mn=10000 g/mol were dissolved in DCM. Of these solutions 100 g was added to 1000 g of solutions of MC in water in a 2 liter beaker within 2 seconds while vigorously stirring at 1000 rpm. PVA with Mn=9000-10000 g/mol obtained from Sigma Aldrich and MC with Mn=63000 g/mol obtained from Colorcon Ltd. were employed.

Within three to four hours continuously stirring vigorously at 1000 rpm at room temperature, essentially all DCM had evaporated. Stirring was discontinued, and the microspheres that had formed were allowed to settle at the bottom of the beaker. The supernatant was removed and the microspheres were washed with water. Using stainless-steel sieves, the microspheres were sieved in the wet state and the fraction with diameters between 38 and 75 micrometer was collected.

The microspheres were vacuum-dried at room temperature, and the yield was determined gravimetrically. Light microscopy (magnification 10×) was employed to analyze the morphology of the obtained microspheres.

A series of experiments, where the nature and the concentration of the surfactant solution were varied, was conducted. The results are presented in Table 5.

Table 5 indicates that using PVA at higher concentrations results in viscous solutions in water that can be used to prepare PCL microspheres by rapidly adding the PCL solution to the vigorously stirred surfactant solution. Very small particles are obtained, and although the morphology of the particles is adequate, the yield of particles in the desired size range that could be recovered is very low. When using MC as a surfactant, the efficiency of the process is significantly better.

Example 7

Experiments of the Invention

PCL Dissolution in Tween Mixtures at Elevated Temperatures Followed by Particle Formation Upon Cooling Upon heating to approximately 80° C. and continuously stirring at 500 rpm, 15 g of PCL with Mn=10000 g/mol was dispersed in 100 ml of a 50/50 wt/wt mixture of Tween 60 and water in a 250 ml glass vessel. Tween 60 is obtained from Sigma Aldrich. The molten polymer droplets are maintained in this dispersed state by stirring for another 2 minutes. While still stirring, the liquid dispersion is then cooled overnight to room temperature. Upon solidification of the dispersed polymer droplets, microspheres are obtained that can be recovered by decantation.

After washing with water, the PCL microspheres were sieved in the wet state using stainless steel sieves and the fraction with sizes between 38 and 75 micrometer was collected. The microspheres were then vacuum dried at room temperature and the yield was determined gravimetrically. A total of 12.1 g of PCL microspheres was collected.

TABLE 5

Preparation of PCL microspheres upon mixing PCL solutions in DCM in viscous surfactant solutions in water while vigorously stirring.

| [PCL] (g/100 g DCM) | surfactant | [surfactant] (wt %) | Viscosity of surfactant solution (cP) | PCL recovered as particles of 38-75 μm (wt %) | PCL particle shapes | PCL particle surfaces |
|---|---|---|---|---|---|---|
| 10 | PVA | 14.7 | 90 | 1.1 | spherical | smooth |
| 10 | MC | 1.1 | 120 | 51.6 | spherical | smooth |
| 20 | MC | 1.1 | 120 | 74.0 | spherical [a] | smooth [a] |

[a] see light microscopy image presented in FIG. 2.

TABLE 6

| | Viscosity of a 50/50 mixture of Tween 60 and water at 80° C. (cP) | PCL recovered as particles of 38-75 μm (wt %) | PCL particle shapes | PCL particle surfaces |
|---|---|---|---|---|
| PCL (g) | | | | |
| 15 | 125 | 80.7 | spherical | smooth |

Preparation of PCL microspheres by cooling PCL solutions in Tween 60 and water mixtures while vigorously stirring.

From this table it can be seen that using relatively viscous Tween 60 and water mixtures, PCL microspheres can be formed from stirred solutions of the polymer at elevated temperatures by cooling.

The invention claimed is:

1. A population of microparticles comprising a polycaprolactone (PCL)-comprising polymer, at least 51.6 weight percent of the microparticles having:
   (i) a diameter between 38 and 75 μm,
   (ii) homogenous density, form and content,
   (iii) essentially spherical and smooth surfaces, and
   (iv) optionally, an active ingredient.

2. The microparticles according to claim 1, wherein the PCL-comprising polymer does not comprise a second monomer selected from the group consisting of glycolide, dioxanone, trimethylene carbonate, lactides, and combinations thereof.

3. The microparticles according to claim 2, wherein the PCL-comprising polymer is a PCL homopolymer.

4. A biodegradable, injectable gel comprising microparticles comprising a polycaprolactone (PCL)-comprising polymer, at least 51.6 weight percent of the microparticles having:
   (i) a diameter between 38 and 75 μm,
   (ii) homogenous density, form and content,
   (iii) essentially spherical,
   (iv) smooth surfaces, and
   (v) optionally comprising an active ingredient.

5. The gel according to claim 4, comprising an anesthetic as the active ingredient.

6. The gel according to claim 4, which is an implant or a filler.

7. A medicament comprising (1) an active ingredient and (2) microparticles comprising a polycaprolactone (PCL)-comprising polymer, at least 51.6 weight percent of the microparticles having:
   (i) a diameter between 38 and 75 μm,
   (ii) homogenous density, form and content,
   (iii) essentially spherical, and
   (iv) smooth surfaces.

8. The medicament according to claim 7, which is a cosmetic.

9. A method of treating a skin abnormality or disfigurement, for controlling bladder function, for controlling gastric reflux, for treating erectile dysfunction, and/or for treating vocal cords, comprising administering to a patient in need thereof a biodegradable, injectable gel comprising microparticles comprising a polycaprolactone (PCL)-comprising polymer, at least 51.6 weight percent of the microparticles having:
   (i) a diameter between 38 and 75 μm,
   (ii) homogenous density, form and content,
   (iii) essentially spherical, and
   (iv) smooth surfaces, and
   (v) optionally comprising an active ingredient.

10. The microparticles according to claim 1, further comprising methyl cellulose.

11. The microparticles according to claim 10, wherein the methyl cellulose has a Mn between 41,000 g/mol and 88,000 g/mol.

12. The microparticles according to claim 1, wherein the PCL-comprising polymer is a linear polymer, a copolymer, a terpolymer or a blend of different types of homo-, co-, and terpolymers.

13. Microparticles comprising a polycaprolactone (PCL)-comprising polymer and having:
   (i) a diameter between 30 and 200 μm,
   (ii) homologous density, form and content,
   (iii) essentially spherical and smooth surfaces, and
   (iv) optionally, an active ingredient,
wherein the microparticles are obtained by using a process comprising:
   (a) solubilizing the PCL polymer in a solvent to form a PCL polymer solution,
   (b) mixing the PCL polymer solution with a liquid comprising between about 1 and about 5 w/w % methylcellulose; and
   (c) forming PCL-comprising microparticles from the solution.

* * * * *